United States Patent [19]

Handjani et al.

[11] Patent Number: 5,137,725
[45] Date of Patent: Aug. 11, 1992

[54] DISPERSION OF LIPIDIC SPHERULES

[75] Inventors: Rose M. Handjani; Alain Ribier, both of Paris, France

[73] Assignee: L'Oreal, Paris, France

[21] Appl. No.: 545,560

[22] Filed: Jun. 29, 1990

Related U.S. Application Data

[63] Continuation of Ser. No. 146,133, filed as PCT FR/87/00128 on Apr. 17, 1987, abandoned.

[30] Foreign Application Priority Data

Apr. 22, 1986 [FR] France ................. 86 05776

[51] Int. Cl.$^5$ .......................... A61K 7/00; A61K 7/48; A61K 7/40; A61K 9/127
[52] U.S. Cl. ....................... 424/401; 424/450; 424/59; 514/844; 514/847; 514/963
[58] Field of Search ................. 264/4.1, 4.3; 428/402.2, 402.22; 424/450, 59, 401; 514/844, 847, 963

[56] References Cited

U.S. PATENT DOCUMENTS

| | | | |
|---|---|---|---|
| 4,217,344 | 8/1980 | Vanlerberghe et al. | 424/450 |
| 4,663,161 | 5/1987 | Mannino et al. | 424/450 X |
| 4,708,861 | 11/1987 | Popescu et al. | 264/4.1 X |
| 4,762,915 | 8/1988 | Kung et al. | 264/4.1 X |
| 4,830,857 | 5/1989 | Handjani et al. | 424/450 |
| 4,853,228 | 8/1989 | Wallach et al. | 424/450 |

FOREIGN PATENT DOCUMENTS

| | | |
|---|---|---|
| 120722 | 10/1984 | European Pat. Off. |
| 2315991 | 1/1977 | France. |
| 155119 | 8/1985 | Japan ................. 424/450 |
| 284000 | 12/1987 | Japan ................. 424/450 |
| 8504880 | 11/1985 | PCT Int'l Appl. |
| 2026340 | 2/1980 | United Kingdom. |

OTHER PUBLICATIONS

Derwent Abstract 85-239352/39 of Japan 60-155,119.
Derwent Abstract 88-024417/04 of Japan 62-284,000.
Huang et al., "Characterization of Antibody Covalently Coupled to Liposomes", Biochim Biophys Acta (716) 140–150, 1982.

Primary Examiner—Robert L. Stoll
Assistant Examiner—John M. Covert
Attorney, Agent, or Firm—Cushman, Darby & Cushman

[57] ABSTRACT

Cosmetic or pharmaceutical composition consisting of a dispersion in an aqueous medium D of lipidic spherules to the lipidic phase of which there is associated at least one lipoprotide free of sulfhydryl function selected amongst the mono- or polyacylated derivatives of amino acids or of polypeptides, wherein the acyle residue R—CO comprises a $C_{13}$-$C_{19}$, hydrocarbonated chain R, at least one of the functions which connects the polypeptidic chain or the amino acid residue to the lipophilic chain being an amide function, the carboxylic functions of the polypeptidic chain or of the amino acid residue being partially or completely neutralized by means of one or a plurality of alkaline cations, an ammonium ion or a substituted ammonium derived from an amine, said lipoprotide or lipoprotides being present in a ratio from 1 to 15% by weight based on the total weight of said lipidic phase.

19 Claims, No Drawings

DISPERSION OF LIPIDIC SPHERULES

This is a continuation of application Ser. No. 07/146,133 filed as PCT FR/87/00128 on Apr. 17, 1987, now abandoned.

The present invention relates to a composition for cosmetic use consisting of an aqueous dispersion of lipidic spherules.

It is known that certain lipids have the property of forming, in the presence of water, mesomorphic phases whose organization state is intermediate between the crystalline state and the liquid state. Among the lipids which give rise to mesomorphic phases it has already been indicated that some can swell in aqueous solution to form spherules dispersed in the aqueous medium, these spherules consisting of multimolecular layers and preferably bimolecular layers.

Dispersions of lipidic spherules have already been described in French Patent No. 2,315,991; these spherules are characterized by their leaflet structure consisting of a plurality of lipidic layers separated from each other by aqueous phase layers; they may thus be used to encapsulate water-soluble active substances in aqueous compartments included between the lipidic layers, and to protect them against external conditions. The lipidic compounds which can be employed for forming such spherules may be ionic compounds, in which case liposomes are obtained, or nonionic compounds, in which case niosomes are obtained.

French Patents No. 2,485,921 and 2,490,504 have also described compositions consisting of an aqueous dispersion of spherules of the abovementioned type with a dispersions of oil provided for in their outer aqueous phase. It has been found that, surprisingly, the presence of lipidic spherules made it possible to stabilize the dispersion of oil and that, in addition, a combined effect of the spherules and of the droplets of oil was obtained with such compositions.

French Patent Number 2,543,018, provides, furthermore, a process for the preparation of unitamellar lipidic vesicles having a mean diameter greater than 1,000 Å.

It will be stressed here that the aqueous dispersions of lipidic vesicles are of very particular interest in cosmetics, where they offer a considerable advantage when compared with the well-known use of emulsions, because they make it possible precisely to avoid the simultaneous use of an emulsifier and of an oil, a combination which may be irritant to the skin. Furthermore, they make it possible to introduce hydrophilic substances into an essentially lipophilic medium, giving rise to a protective action of these substances in respect of various possible agents of change, such as oxidizing agents.

When liposomes or niosomes are prepared, various additives may be combined with the ionic or nonionic lipidic compounds, in order to modify the permeability or the surface charge of the spherules. A certain number of these additives have been mentioned in this connection in the abovementioned French patents. It is known that the incorporation of molecules carrying electrical charges in the walls of the vesicles, liposomes or niosomes affects the properties of these multilayers. The role of the charged lipids is to improve the stability of the vesicles by preventing their flocculation and, consequently, their fusion, even in the presence of electrolytes, and to permit the increase in the degree of encapsulation of water-soluble substances by increasing the thickness of the aqueous leaflets which separate the lipidic multilayers.

In order to improve the topical properties of these lipidic vesicles, it may be considered appropriate to incorporate in the lipidic phase which forms part thereof, compounds which have a beneficial effect on the cutaneous coating, such as polypeptides or compounds containing polypeptide fractions. However, it is known that, as a general rule, polypeptides have a destabilizing effect on the lipidic vesicles, with the inconvenient consequence of an increase in the permeability.

Surprisingly, the applicants company have found that the use of a specific group of lipoproteinic compounds as additives to the lipidic phase of the spherules leads to the required improvement in the topical effect without the finding of a marked and prohibitive increase in the premeability, provided, however, that a specified range of proportions is adhered to in respect of these lipoproteins.

In parallel with this surprising maintenance of the encapsulation capacity of lipidic vesicles, the dispersion stability effect is retained.

The lipoproteins according to the invention all have, on the one hand, a lipidic portion by which they are incorporated into the vesicular membrane and, on the other hand, a proteinic part which is directed towards the outside of the said membrane and which will thus be capable, during application to the cutaneous coating or to the hair, of acting directly on these.

The subject of the present invention is therefore the new industrial product constituted by a cosmetic or pharmaceutical composition consisting of a dispersion, in an aqueous medium D, of lipidic spherules constituted by organized molecular layer encapsulating an aqueous phase E, the constituent lipid(s) of the said layers being one or more ionic or nonionic amphiphile(s) which is characterized in that the lipidic phase itself of the said spherules is combined with at least one lipoprotein free from sulphydryl functional group and chosen from mono- or polyacylated derivatives of amino acids or of polypeptides in which the acyl residue R—CO contains a $C_{13}$–$C_{19}$ hydrocarbon chain R, at least one of the functional groups which connects the polypeptide chain or the amino acid residue to the lipophile chain being an amide functional group, it being possible for the carboxylic functional groups of the polypeptide chain or of the amino acid residue to be, where appropriate, partially or completely neutralized by one or more alkali metal cations, or an ammonium ion or substituted ammonium ion derived from an amine, the said lipoprotein(s) being present in a proportion of 1 to 15% by weight relative to the total weight of the lipidic phase itself.

In this definition, throughout the description, and in the claims, "lipidic phase itself" is the name given to the quantity of the lipids which constitute the walls of the vesicles.

Preferably, the acyl residue(s) of the lipoproteins employed is (or are) chosen from the palmitoyl, myristoyl, stearoyl, oleoyl, linoleoyl and linolenoyl residues.

The proteinic chain of the lipoproteins employed is derived particularly from collagen or from hydroxyproline.

Among the individual lipoproteins which can be employed for implementing the present invention, there may be mentioned the collagenic palmitoyl lipoamino acid, the O,N-dipalmitoyl derivative of hydroxyproline, hydroxyproline linoleate, sodium stearoylglutamate, collagen stearoyl tripeptide and collagen oleoyl tetra- and pentapeptide.

For range of proportions which is specified for the lipoproteins (1 to 15% by weight relative to the lipidic phase itself) results from an optimum compromise between obtaining an appreciable cosmetic effect of the lipoproteins introduced and the retention of the impermeability of the vesicles within acceptable limits. If the proportion of lipoproteins were chosen with a value of less than 1%, the cosmetic effect would no longer be observed. On the other hand, were this proportion to exceed 15%, the permeability of the vesicles would be too high to enable them to be suitably used.

Any of the processes known previously and described may be employed in order to produce the dispersion of the lipidic spherules in the aqueous phase D.

It is possible, for example, to employ the process which consists in dissolving the lipids in a volatile solvent, in forming a thin film of lipids on the walls of a flask by evaporating the solvent, in introducing into the said flask the aqueous phase E to be encapsulated and in agitating the mixture mechanically until a dispersion of spherules of the desired size is obtained; in this case, the aqueous phases D and E are necessarily identical.

It is also possible to employ the process described in French Patent No. 2,315,991, which consists in forming a planar lamellar phase by introducing the aqueous phase to be encapsulated E into the liquid lipids at a temperature slightly above the melting temperature of the lipids, in then adding to the lamellar phase obtained an aqueous dispersion phase D, which may be identical or not identical with the aqueous phase E, and in agitating vigorously, for example mechanically, in order to produce the conversion of the planar lamellar phase into a dispersion, in the aqueous phase D, of lipidic spherules encapsulating the aqueous phase E. According to the means employed to produce the dispersion (ultradisperser, homogenizer and/or ultrasonics) and depending on the duration of agitation (from 15 minutes to a few hours), spherules are obtained, whose means diameter varies approximately from 0.025 to 5 microns.

The abovementioned process is particularly suitable when it is desired to employ multilamellar spherules. In the case where unilamellar spherules are desired, the process described in French Patent Number 2,543,018 may be employed to prepare them; according to this process, the lipids intended to form the leaflet of the vesicles are dissolved in at least one water-insoluble solvent; the lipidic solution in the liquid state is packaged in a receptacle, at a pressure $P_1$ and at a temperature $\theta_1$; the aqueous phase to be encapsulated E is packaged at a pressure $P_2$ and at a temperature $\theta_2$, and the lipidic solution is injected into the aqueous phase so that the solvents(s) of the lipidic solution vaporize(s) on coming into contact with the said aqueous phase, the said injection being carried out at a reduced flow rate in order to form droplets initially, the pressure $P_2$ being lower than the pressure $P_1$ and lower than the vapor pressure of the solvent(s) in the said droplets at the temperature $\theta_2$.

The lipoproteins according to the invention may be added at any time before the formation of the vesicles, that is to say, during the passage through the formation of a lamellar phase, either before the preparation of the said lamellar phase, or after.

The lipids employed for the preparation of the spherules are ionic or nonionic amphiphiles of natural or synthetic origin comprising, per molecule, one or more linear or branched, saturated or unsaturated, hydrocarbon chain(s containing particularly from 8 to 30 carbon atoms, such as the oleyl, lanolyl, tetradecyl, hexadecyl, isostearly, lauryl or alkylphenyl chains, and one or more hydrophilic group(s) taken from the hydroxyl, ether, carboxyl, phosphate and amine groups.

Among the ionic amphiphiles, the use of natural phospholipids (for example egg or soya lecithin or sphingomyelin), or of synthetic phospholipids (for example dipalmitoylphosphatidylcholine or hydrogenated lecithin) is preferred; it is also possible to employ amphoteric compounds containing two lipophile chains or a combination of two long-chain organic ions of opposite signs, as well as anionic compounds.

Among the anionic compounds, mention will be made of those described in the Luxembourg Patent Application No. 85/971 filed on Jun. 23, 1985 and represented by the formula:

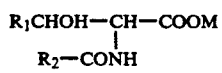

in which formula:
$R_1$ denotes a $C_7$-$C_{21}$ alkyl or alkenyl radical;
$R_2$ denotes a $C_7$-$C_{31}$ saturated or unsaturated hydrocarbon radical; and
M denotes H, Na, K, $NH_4$ or a substituted ammonium ion derived from an amine.

The anionic compounds defined in the preceding paragraph may be obtained by the preparative process referred to in French Patent Application 2,588,256.

In the case of the nonionic amphiphiles it is preferred that the hydrophilic groups should be polyoxyethylenated or polyglycerolated groups, or groups derived from esters of polyols, oxyethylenated or otherwise, or else hydroxyamide derivatives. Advantageously, these nonionic lipidic compounds are chosen from the group consisting of
linear or branched polyglycerol ethers, of formulae:

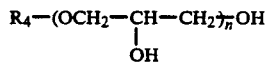

and

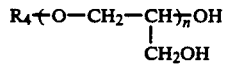

respectively, $\overline{n}$ being a means statistical value of between 1 and 6, $R_4$ being a saturated or unsaturated, linear or branched aliphatic chain containing from 12 to 30 carbon atoms, the hydrocarbon radicals of lanolin alcohols or the 2-hydroxyalkyl residues of long-chain α-diols;
linear or branched polyglycerol ethers containing two fatty chains;
polyoxyethylenated fatty alcohols;
polyoxyethylenated sterols;
polyol ethers;
esters of polyols, oxyethylenated or otherwise and, in particular, polyoxyethylenated sorbitol esters;
glycolipids of natural or synthetic origin, for example cerebrosides;
hydroxyamides such as those described in Luxembourg Patent Application No. 85/971 filed on Jun. 23, 1985 and represented by the formula:

$$R_1-CHOH-CH-COA$$
$$\phantom{R_1-CHOH-CH}|$$
$$\phantom{R_1-CHOH}R_2-CONH$$

in which formula:

$R_1$ denotes a $C_7$–$C_{21}$ alkyl or alkenyl radical;

$R_2$ denotes a $C_7$–$C_{31}$ saturated or unsaturated hydrocarbon radical;

COA denotes a group chosen from the following two groups:
a residue $$CON-B$$
$$\phantom{CON}|$$
$$\phantom{CON}R_3$$

B being a radical derived from mono- or polyhydroxylated primary or secondary amines and $R_3$ denoting a hydrogen atom or a methyl, ethyl or hydroxyethyl radical;

COOZ, Z denoting the residue of a $C_3$–$C_7$ polyol.

In a known manner, various other additives may be combined with the lipidic compounds in order to modify the permeability of a surface charge of the spherules. In this connection, mention will be made of the optional addition of long-chain alcohols and diols, of sterols, for example cholesterol and β-sitosterol, of long-chain amines, of hydroxylatkylamines, of polyoxyethylenated fatty amines, of long-chain aminoalcohol esters, of their salts, of phosphoric esters of fatty alcohols, for example sodium dicetylphosphate and of alkylsulphates, for example sodium cetylsulphate, and of ionic derivatives of sterols.

From 0.5 to 25% by weight of amphiphile(s) relative to the total weight of the dispersion of spherules to be obtained may be advantageously employed to form the dispersion of spherules.

Arrangements may be made for the walls of the spherules to contain at least one active liposoluble substance such as, for example, a keratolytic agent such as retinoic acid, or an anti-inflammatory agent such as β-methasone 17-valerate, or else an antioxidant such as vitamin E and its acetate or ascorbyl palmitate, which is of particular interest when topical applications are envisaged.

It is also possible to arrange for the aqueous phase E to be encapsulated in the spherules to be an aqueous solution of active substance, preferably isoosmotic relative to the phase D of the dispersion. The D and E phases may be identical.

The aqueous phase E encapsulated in the spherules or the outer aqueous phase D contains, for example, at least one water-soluble cosmetic substance taken from the group consisting of humectants such as glycerine, sorbitol, pentaerythritol, inositol, pyrrolidonecarboxylic acid and its salts; artificial tanning agents such as dihydroxy acetone, erythrulose, glyceraldehyde, γ-dialdehydes such as tartaric aldehyde, optionally combined with other skin-coloring agents; antisolar agents, antiperspirants, deodorants, astringents; freshening, tonic, cicatrizing, keratolytic or depilatory products; extracts of animal or plant tissues; perfumed waters, water-soluble colorants, antidandruff agents, antiseborrhoeic agents, oxidizing agents such as hydrogen peroxide, and reducing agents such as thioglycolic acid and its salts.

In the case of a composition which may be employed in pharmacy, the aqueous phase encapsulated in the spherules or the outer aqueous phase D preferably contains at least one product taken from the group consisting of vitamins, hormones, enzymes, such as superoxide dismutase, vaccines, antiinflammatories such as hydrocortisone, antibiotics and bactericides.

Provision may also be made for the aqueous phase D surrounding the spherules to contain at least one water-immiscible liquid phase L dispersed in the said aqueous phase D. This water-immiscible liquid phase L may be an oil or a constituent taken from the group consisting of hydrocarbons, halogenated hydrocarbons, polysiloxanes, organic acid esters, ethers and polyethers. Advantageously, the quantity of water-immiscible liquid phase L dispersed in the aqueous phase D is between 2 to 70% by weight relative to the total weight of the composition, the relative weight proportion of amphiphile lipid constituent(s) of spherules relative to the dispersed water-immiscible liquid phase(s) being between 0.02/1 and 10/1.

The oil used in order to be dispersed in the aqueous phase D is advantageously taken from the group consisting of the esters of fatty acids and of polyols, especially liquid triglycerides, and of esters of fatty acids and of branched alcohols of formula $R_5$-COOR$_6$, in which formula $R_5$ denotes the residue of a higher fatty acid containing from 7 to 19 carbon atoms and $R_6$ denotes a branched hydrocarbon chain containing from 3 to 20 carbon atoms. In such case, if the oil is an ester of fatty acids and of polyols, it is preferable that it be chosen from the group consisting of sunflower, corn, soya, marrow, grapeseed, jojoba or sesame oils and glycerol tricaprocaprylate; if, on the other hand, the oil is higher ester of fatty acids and of a branched alcohol, it is preferable that the said oil be prucellin oil.

In order to form the water-immiscible liquid phase L it is also possible to choose, advantageously, hexadecane, liquid paraffin, perhydrosqualene, perfluorotributylamine, perfluorodecahydronaphthalene and volatile silicone oil.

Provision may also be made for the aqueous phase D, which surrounds the spherules, to contain at least one adjuvant taken from the group consisting of opacifiers, gelling agents, flavors, perfumes, sunscreens and colorants, it being possible for those of these adjuvants which are liposoluble to be dissolved in the water-immiscible liquid phase L dispersed in the aqueous phase D, in the case where such a dispersion is employed.

If the water-immiscible liquid dispersed and added to the continuous aqueous phase which surrounds the spherules is to contain dissolved adjuvants, the dissolving of these adjuvants is carried out before the dispersion is produced.

Such adjuvants may be, for example, sunscreens, such as 2-ethylehexyl para-dimethylaminobenzoate, or substances intended to improve the condition of dry or senile skins, especially nonsaponifiable materials such as the nonsaponifiable materials from soya, avocado, tocopherols, vitamins E and F, and antioxidants.

The dispersion of oil in water which constitutes the outer medium of the dispersion of spherules may contain at least one additive, particularly a gelling agent or a perfume. The additive is added to the dispersion at the same time as the oil. The gelling agent may be introduced at a concentration ranging between 0.1 and 2%, these percentages being expressed on a weight basis relative to the total weight of the composition. Among the gelling agents which may be employed there may be mentioned cellulose derivatives such as hydroxyethyl cellulose, synthetic polymers, seaweed derivatives such as satiagum or natural resins such as tragacanth. As gelling agents it is preferable to employ hydroxyethyl cellulose, the crosslinked polyacrylic acid sold by Goodrich under the trade name "Carbopol 940", satiagum or else tragacanth.

When a composition containing a dispersion of water-immiscible liquid(s) is produced, it is found that this dispersion is stable without the use of emulsifier.

If the dispersion of spherules contains spherules of a number of types, for example niosomes and liposomes, the two types of spherules are prepared separately and the two dispersions are mixed.

In order to illustrate the subject of the present invention better an indication will now be given of the results of tests demonstrating that the introduction of lipoproteins according to the invention into the lipidic phase of spherules in dispersion in water maintains a permeability and a degree of encapsulation which are wholly acceptable in the case of these spherules, as long as the upper limit of the specified range of the percentages of these lipoproteins is not exceeded.

These tests are summarized in the table below.

TABLE

| X | Lipidic phase consisting A, Ch and X, the weight ratio A/Ch being 1/1. Weight percentage of X relative to (A + Ch) | Swelling with glucose in μg per mg of lipidic phase | Permeability (%) after (n) days | | |
|---|---|---|---|---|---|
| | | | (n) = 0 | (n) = 8 | (n) = 15 |
| B | 5 | 9.1 | 0 | 3 | 8 |
| | 10 | 9.5 | 0 | 4 | 9 |
| | 15 | 8.5 | 1 | 9 | 14 |
| | 20 (*) | 5.8 | 13 | 20 | 24 |
| C | 5 | 6.2 | 1 | 3 | 6 |
| | 10 | 6.7 | 1 | 25 | 34 |
| | 20 (*) | 3.5 | 31 | 42 | 57 |
| D | 10 | 11.8 | 10 | 16 | 18 |
| E | 10 | 14.5 | 5 | 5 | 5 |
| F | 10 | 9.6 | 10 | 13 | 14 |
| G | 10 | 9.8 | 3 | 11 | 17 |

(*) Comparative experiment not forming part of the invention

In this table, the abbreviations A, Ch, B, C, D, E, F and G have the following meanings, respectively:

A = Nonionic lipid denoted by the following formula:

$$R\mathord{-}(OCH_2\mathord{-}CH)_{\overline{n}}OH$$
$$| $$
$$CH_2OH$$

in which $R = C_{16}H_{33}$ and n is a mean statistical value equal to 3.

Ch = Cholesterol

B = Collagenic palmitoyl lipoamino acid, denoted by the formula:

$$CH_3-(CH_2)_{14}-CO-NH-CH-COOH$$
$$|$$
$$R_{Coll}$$

in which $R_{Coll}$ is the collagen polypeptide residue, this product being marketed by Rhône-Poulenc under The name "PCo".

C = The O,N-dipalmitoyl derivative of hydroxyproline, denoted by the formula:

$$CH_3-(CH_2)_{14}-COO-\underset{\underset{H_2C}{|}}{\overset{\overset{H}{|}}{C}}-CH_2$$
$$H_2C \quad CH-COOH$$
$$\diagdown N \diagup$$
$$|$$
$$CO-(CH_2)_{14}-CH_3$$

of molecular weight 607, the lipidic and proteinic fractions representing 79 and 21% by weight respectively, this acid being marketed by Rhône-Poulenc under the name "D.P.H.P.".

D = Hydroxyproline linoleate marketed under the name "Aminoefaderma" by Vevy.

E = Sodium stearoylglutamate marketed by Ajinomoto under the name "Acylglutamate H.S.11"

F = Collagen stearotyltripeptide marketed under the name "Lexein A 200" by Inolex.

G = Collagen oleoyltetra- and pentapeptide marketed under the name "Lamepon L PO" by Grünau.

A few examples of preparation making use of the invention and a few examples of formulation illustrating the use of the dispersions of spherules according to the invention will be given below.

The preparation of the cosmetic or pharmaceutical formulations given in the examples below is carried out in 1 to 2 stages.

In a first stage, an aqueous dispersion is manufactured according to the process described in French Patent 2,315,991.

The aqueous dispersion of lipidic spherules is prepared from:
a nonionic or anionic or amphoteric amphiphile lipid,
a lipoprotein containing one or more acidic functional groups which are free or neutralized in the form of salts,
a sterol, optional, and preferably cholesterol,
optional active substances of liposoluble nature and/or of water-soluble nature and of demineralized water.

In a second stage, optional, depending on the cosmetic or pharmaceutical nature of the formulation, a water-immiscible liquid phase may be added to the outer medium.

It is also possible to add various cosmetic additives such as perfume and gelling agents, for example.

EXAMPLE 1

Care Cream for Dry Skins

1st stage of preparation

The following materials are weighed in a stainless steel beaker:

| | |
|---|---|
| nonionic amphiphilic lipid of formula | 3.5 g |

$$R-(OCH_2-CH)_{\bar{n}}-OH$$
$$\phantom{R-(OCH_2-}CH_2OH$$

(in which formula R is a hexadecyl radical and $\bar{n}$ has a mean statistical value equal to 3)

| | |
|---|---|
| cholesterol | 3.5 g |

The mixture of these two materials is produced by melting at the temperature of 110° C. under a nitrogen atmosphere, and then the temperature of the molten mixture is brought down to 80° C. 1 g of the collagenic palmitoyl lipoamino acid marketed under the reference "PCO" by Rhône-Poulenc, of formula

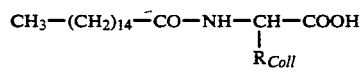

in which formula $R_{coll}$ is a collagen polypeptide residue, is then added.

After the mixture of the three materials has been homogenized at the temperature of 80° C. 3 g of glycerine dissolved in 20 g of demineralized water are added.

The mixture obtained is homogenized at the temperature of 80° C.

| | |
|---|---|
| methyl para-hydroxybenzoate (stabilizer) | 0.3 g |
| demineralized water | 22.5 g |

The mixture of homogenized at the temperature of 80° C. by means of a "Virtis" ultradisperser until the mean size of the vesicles obtained is 0.5 micron.

2nd stage of preparation 25 g of sesame oil are added to the mixture obtained. The whole is subjected to the action of a "Virtis" ultradisperser until the globules of oil have a mean diameter of about 1 micron.

Lastly, the following materials are added:

| | |
|---|---|
| perfume | 0.4 g |
| crosslinked polyacrylic acid sold by Goodrich under the trade name "Carbopol 940" | 0.4 g |
| triethanolamine | 0.4 g |
| demineralized water | 20.0 g |

This cream, applied in topical use once daily on dry-skinned individuals, gives satisfactory results after 20 days' application.

EXAMPLE 2

Care Base for Fingernails the following materials are weighed in a stainless steel beaker:

| | |
|---|---|
| nonionic amphiphilic lipid of formula | 8.5 g |

$$R-(OCH_2-CH)_{\bar{n}}-OH$$
$$\phantom{R-(OCH_2-}CH_2OH$$

(in which formula R is a hexadecyl radical and $\bar{n}$ has a mean statistical value equal to 3)

| | |
|---|---|
| cholesterol | 8.5 g |

The mixture of these two materials is produced by melting at the temperature of 110° C. under a nitrogen atmosphere, and the temperature of the molten mixture is then brought down to 70° C. and 3 g of sodium stearoyl-glutamate sold by Ajinomoto under the name "Acylglutamate HS11" are added.

After the mixture of the three materials has been homogenized at the temperature of 70° C., 5 g of glycerine dissolved in 50 g of demineralized water are added. The mixture obtained is homogenized at the temperature of 70° C. The following materials are then added:

| | |
|---|---|
| methyl para-hydroxybenzoate (stabilizer) | 0.3 g |
| demineralized water | 24.3 g |
| perfume | 0.4 g |

The mixture is homogenized at the temperature of 70° C. with the aid of a "Virtis" ultradisperser until the mean size of the vesicles obtained is about 0.3 micron.

After twice-daily application of the care base for fingernails, at the end of several days, a smoothing and a hardening of the surface of the fingernails are observed.

EXAMPLE 3

Concentrate for the Treatment of Irritated Skins the following materials are dissolved in 200 ml of a solvent mixture (chloroform/methanol in the ratio 2/1) in a 1-liter round-bottomed flask:

| | |
|---|---|
| soya lecithin sold under the trade name "Epikuron E 200" by Lukas Meyer | 12.0 g |
| cholesterol | 4.0 g |
| DL-α-tocopherol | 1.0 g |
| hydroxyproline linoleate (product marketed under the name "Amino-efaderma" by Vevy | 1.5 g |

The solvent is evaporated off with a rotary evaporator and the last traces of solvent are removed by using a rotary pump for one hour. The combination of lipids obtained is placed in contact with 40 g of demineralized water mixed with 3 g of glycerine. The mixture is homogenized at the temperature of 40° C.

The following materials are then added:

| | |
|---|---|
| methyl para-hydroxybenzoate (stabilizer) | 0.3 g |
| demineralized water | 37.5 g |
| perfume | 0.7 g |

The whole is subjected to the action of an ultradisperser of the "Virtis" type until the mean size of the vesicles obtained is less than a micron.

The fluid dispersion obtained may be applied to the skin by spraying from a pump bottle.

This cream, employed as a topical application twice daily on subjects with an irritated skin affected by acne, reduces the irritation after one or two weeks' application.

EXAMPLE 4

Liposerum for Hardening the Skin

The following materials are weighed in a stainless steel beaker:

| | |
|---|---|
| nonionic amphiphilic lipid of formula $R-(OCH_2-\underset{\|}{CH})_{\overline{n}}OH$ $\qquad CH_2OH$ (in which formula R is a hexadecyl radical and $\overline{n}$ is a mean statistical value equal to 3) | 5.4 g |
| cholesterol | 5.4 g |

The mixture of these two materials is produced by melting at the temperature of 110° C. under a nitrogen atmosphere, and then the temperature of the molten mixture is brought down to 75° C. an 1.2 g of a collagen stearoyl tripeptide marketed by Inolex under the trade name "Lexein A 200" is added. The mixture is homogenized at the temperature of 75° C.

A part of the aqueous phase consisting of the following is then added:

| | |
|---|---|
| glycerine | 3.0 g |
| demineralized water | 17.0 g |
| aqueous solution obtained by grinding animal placental tissues, marketed by Gattefosse under the trade name "Phylderm" | 20.0 g |

The mixture obtained is homogenized at the temperature of 70° C.

The temperature is brought down to 60° C. and 20 g of an aqueous solution containing 1% of monomethyl-trisilanol mannuronate sold by Exymol under the trade name "Algisium" are added. The mixture is homogenized at the temperature of 60° C. with the aid of a "Virtis" ultradisperser until the mean size of the vesicles obtained is about 0.5 micron. At this stage of manufacture, the dispersion is cooled to ambient temperature and its pH is adjusted to 5.5 by adding an aqueous 0.1 N sodium hydroxide solution.

0.15 g of a stabilizer sold by Rohm and Haas under the trade name "Kathon CG", dissolved in 1 g of demineralized water, is then added. 10 g of an aqueous solution containing 5% of bovine serum albumin, marketed by Silab are then added. The mixture obtained is homogenized and 6 g of volatile silicone oil are added. The whole is subjected to the action of an ultradisperser until the globules of oil have a mean diameter of less than a micron.

Lastly, the following materials are added;

| | |
|---|---|
| polyglucose containing a linear chain sold by Alban Muller under the trade name "Amigel Poudre" | 0.1 g |
| demineralized water q.s. | 100 g |

After application twice daily for 3 weeks, a hardening of the skin is noted.

EXAMPLE 5

Milk for the Care of Dry Skins

1st stage of preparation

The following materials are weighed in a stainless steel beaker:

| | | |
|---|---|---|
| a) | nonionic amphiphile lipid of formula: 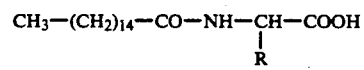 | 7.0 g | in which:
R is a dodecyl radical;
R' is an equimolar mixture of tetradecyl and hexadecyl radicals; and
$\overline{n}$ has a mean statistical value determined by nuclear magnetic resonance equal to 5.5

| | | |
|---|---|---|
| b) | collagenic palmitoyl lipoamino acid marketed under the reference "PCO" by Rhône-Poulenc, of formula $CH_3-(CH_2)_{14}-CO-NH-\underset{\underset{R}{\|}}{CH}-COOH$ | 1 g | in which R is an amino acid obtained by the hydrolysis of collagen.

After homogenization at 45° C., 3 g of glycerine dissolved in 20 g of demineralized water are added. The mixture obtained is homogenized at 90° c.; 0.3 g of methyl para-hydroxybenzoate (stabilizer) dissolved in 37.4 g of demineralized water are then added.

The mixture is homogenized at 40° C. by means of a "Virtis" ultradisperser until the mean size of the spherules obtained is 0.2 micron.

1.3 g of aqueous normal sodium hydroxide solution are then added with stirring.

2nd stage of preparation 15.0 g of sesame oil are added. The whole is subjected to the action of the "Virtis" ultradisperser so that the outer phase of the oil dispersion has globules of oil whose means diameter is about 1 micron.

Lastly, the following materials are added:

| | |
|---|---|
| perfume | 0.4 g |
| crosslinked polyacrylic acid sold under the trade name "Carbopol 940" by Goodrich | 0.4 g |
| triethanolamine | 0.4 g |
| demineralized water | 13.8 g |

This milk, applied in topical use once daily on dry-skinned subjects, gives satisfactory results after two weeks' application.

EXAMPLE 6

Care Cream for Skins Affected by Acne

The whole preparation of this cream was carried out in the yellow light of a sodium vapor lamp.

1st stage of preparation

The following materials are dissolved in 200 ml of a solvent mixture (chloroform/methanol in the ratio 1/1), in a 1-liter round-bottomed flask:

| | |
|---|---|
| nonionic lipid of formula: $R-(O-CH_2-CH)_{\bar{n}}-OH$ with $CH_2OH$ branch in which R is a hexadecyl radical and $\bar{n}$ has a mean statistical value equal to 3 | 3.8 g |
| cholesterol | 3.8 g |
| acyl glutamate $HS_{11}$ marketed by Ajinomoto, of formula: $Na^+ {}^-OOC-CH_2-CH_2-CH-COO^{-+}H$ with $NH-COR$ branch where R is a stearyl radical | 0.4 g |
| retinoic acid sold by Roche under the trade name "Tretinoine" | 0.025 g |

The solvent is evaporated off with a rotary evaporator and the last traces of solvent are removed with a rotary pump for 1 hour.

The combination of lipids obtained is placed in contact with 20.0 g of demineralized water mixed with 3.0 of glycerine. The mixture obtained is homogenized at 80° C. 0.3 g of methyl parahydroxy-benzoate (stabilizer) dissolved in 38.675 g of demineral-ized water is then added.

The mixture is homogenized at 60° C. by means of a "Virtis" ultradisperser until the mean size of the spherules obtained is about 0.3 micron.

2nd phase of preparation 15 g of glycerol tricaprocaprylate are added.

the whole is subjected to the action of the "Virtis" ultradisperser so that the outer phase of the oil dispersion has oil globules whose mean diameter is about 1 micron.

Lastly, the following substances are added:

| | |
|---|---|
| perfume | 0.4 g |
| crosslinked polyacrylic acid sold under the trade name "Carbopol 940" by Goodrich | 0.4 g |
| triethanolamine | 0.4 g |
| demineralized water | 13.8 g |

This cream, employed in topical application twice daily of subjects whose skin is affected by acne, enables appreciable improvement to be obtained after two weeks' application.

EXAMPLE 7

Aqueous Dispersion of Spherules for Face Care

The following materials are weighed in a stainless steel beaker:

| | |
|---|---|
| nonionic amphiphile lipid employed in Example 5 | 5.6 g |
| cholesterol | 1.6 g |
| collagenic palmitoyl lipoamino acid marketed under the reference "PCO" by Rhône-Poulenc, of formula $CH_3-(CH_2)_{14}-CO-NH-CH-COOH$ with R branch in which R is an amino acid obtained by the hydrolysis of collagen | 0.8 g |

After homogenization at 95° C., 5.0 g of glycerine dissolved in 20.0 g of demineralized water are added. The mixture obtained is homogenized at 95° C.

0.3 g of methyl para-hydroxybenzoate (stabilizer), dissolved in 50.7 g of demineralized water, are then added.

The mixture is homogenized at 40° C. by means of a "Virtis" ultradisperser until the means size of the spherules obtained is 0.2 micron. 1.0 g of an aqueous normal sodium hydroxide solution is then added with stirring.

Lastly, the following substances are added:

| | |
|---|---|
| perfume | 0.2 g |
| crosslinked polyacrylic acid sold under the trade name "Carbopol 940" by Goodrich | 0.2 g |
| triethanolamine | 0.2 g |
| demineralized water | 14.4 g |

This dispersion, employed in topical application for face care one daily, gives a highly satisfactory result after two weeks' application.

EXAMPLE 8

Vesicular Corticoid Preparation

The following materials are weighed in a stainless steel beaker:

| | |
|---|---|
| nonionic amphiphilic lipid employed in Example 5 | 7.6 g |
| collagenic palmitoyl lipoamino acid of formula $CH_3-(CH_2)_{14}-CO-NH-CH-COOH$ with R branch in which R is an amino acid obtained by the hydrolysis of collagen (marketed under the name "PCO" by Rhône-Poulenc) | 0.4 g |
| β-methasone 17-valerate (product marketed by Larks) | 0.08 g |

The mixture of these three products is produced by melting at 90° C. 20 g of demineralized water are added. The mixture obtained is homogenized at 90° C.

The following materials are then added:

| | |
|---|---|
| methyl para-hydroxybenzoate (stabilizer) | 0.3 g |
| glycerine | 5.0 g |
| demineralized water | 52.02 g |

The mixture is homogenized at 40° C. by means of an ultradisperser of the "Virtis" type until the means size of the vesicles obtained is 0.2 micron.

0.5 g of an aqueous normal sodium hydroxide solution is then added with stirring.

Lastly, the following materials are added:

| | |
|---|---|
| crosslinked polyacrylic acid sold under the trade name "Carbopol 940" by Goodrich | 0.4 g |
| triethanolamine | 0.4 g |
| demineralized water | 13.3 g |

This preparation, employed in topical application twice daily on subjects affected by dermatitis, enables an appreciable improvement to be found after a fey days' application.

EXAMPLE 9

Aqueous Dispersion of Lipidic Vesicles

The following materials are dissolved in 200 ml of a solvent mixture (chloroform/methanol in the ratio 1/1) in a 1-liter round-bottomed flask:

| | |
|---|---|
| nonionic amphiphilic lipid employed in Example 5 | 7.6 g |
| collagenic palmitoyl lipoamino acid of formula $CH_3-(CH_2)_{14}-CO-NH-\underset{R}{CH}-COOH$ in which R is an amino acid obtained by the hydrolysis of collagen (marketed under the name "PCO" by Rhône-Poulenc) | 0.4 g |
| α-tocopherol acetate (product marketed by Roche) | 0.2 g |
| α-tocopherol (product marketed by Roche) | 0.2 g |
| ascorbyl palmitate (product marketed by Roche) | 0.4 g |

The solvent is evaporated off with a rotary evaporator and the last traces of solvent are removed with a rotary pump for 1 hour. The combination of lipids obtained is placed in contact with 20 g of demineralized water. The mixture obtained is homogenized at 90° C.

The following materials are then added:

| | |
|---|---|
| methyl para-hydroxybenzoate (stabilizer) | 0.3 g |
| glycerine | 5.0 g |
| demineralized water | 50.8 g |

The mixture is homogenized at 40° C. by means of a "Virtis" ultradisperser until the means size of the vesicles obtained is 0.2 micron.

0.5 g of aqueous normal sodium hydroxide solution is then added with stirring.

Lastly, the following materials are added:

| | |
|---|---|
| crosslinked polyacrylic acid sold under the name "Carbopol 940" by Goodrich | 0.4 g |
| triethanolamine | 0.4 g |
| demineralized water | 13.8 g |

This dispersion, employed in topical application once daily on subjects who have a skin exhibiting ;some signs of aging, gives satisfactory results after four weeks' application.

We claim:

1. A cosmetic or pharmaceutical composition comprising a dispersion, in an aqueous medium D suitable for topical application to the skin and nails, of lipid spherules constituted by organized molecular layers encapsulating in aqueous phase E, the constituent lipid of the said layers being nonionic amphiphiles, wherein the lipidic phase itself of the said spherules is combined with at least one lipoprotein free from any sulphydryl functional group and chosen from mono- or polyacrylated derivatives of amino acids or of polypeptides in which the acyl reside R—CO contains a $C_{13}$-$C_{19}$ hydrocarbon chain R, at least one of the functional groups which connects the polypeptide chain on the amino acid residue to the lipoprotein chain being amide functional group, it being possible for the carboxylic functional groups of the polypeptide chain or of the amino acid residue to be partially or completely neutralized by one or more alkali metal cations, or an ammonium ion or substituted ammonium ion derived from an amine, the said lipoprotein being present in a proportional of 1 to 15% by weight relative to the total weight of the said lipid phase itself.

2. Composition according to claim 1, characterized in that the acyl residue of the lipoproteins employed is chosen from the myristoyl, palmitoyl, stearoyl, oleoyl, linoleoyl and linolenoyl residues.

3. Composition according to claim 1, characterized in that the nonionic amphiphile lipids are taken from the group consisting of:

linear or branched polyglycerol ethers, of formulae, $$R_4-(OCH_2-\underset{OH}{CH}-CH_2)_{\overline{n}}OH$$

and $$R_4-(O-CH_2-\underset{CH_2OH}{CH})_{\overline{n}}OH$$

respectively, $\overline{n}$ being a mean statistical value of between 1 and 6, $R_4$ denoting a saturated or unsaturated, linear or branched aliphatic chain containing 12 to 30 carbon atoms, the hydrocarbon radicals of lanoline alcohols or the 2-hydroxyalkyl residues of long-chain α-diols;

linear or branched polyglycerol ethers containing two fatty chains;

polyoxyethylenated fatty alcohols or polyoxyethylenated sterols;

polyol ethers;

esters of polyols, oxyethylenated or otherwise;

glycolipids of natural or synthetic origin;

the hydroxyamides denoted by the formula:

$$R_1-CHOH-\underset{R_2-CONH}{CH}-COA$$

in which formula:

$R_1$ denotes a $C_7$-$C_{21}$ alkyl or alkenyl radical;

$R_2$ denotes a $C_7$-$C_{31}$ saturated or unsaturated hydrocarbon radical;

COA denotes a group chosen from the following two groups:

a residue $$\underset{R_3}{CON-B}$$

B being a radical derived from mono- or polyhydroxylated primary or secondary amines and $R_3$ denoting a hydrogen atom or a methyl, ethyl or hydroxyethyl radical;

COOZ, Z denoting the residue of a $C_3$–$C_7$ polyol.

4. Composition according to claim 1, characterized in that the amphiphiles intended to form the spherules are combined with additives taken from the group consisting of long-chain alcohols and diols, of sterols, of long-chain amines, of hydroxyalkylamines, of polyoxyethylenated fatty amines, of long-chain amino alcohol esters, and their salts, of phosphoric esters of fatty alcohols, of alkyl sulphates, and of ionic sterol derivatives.

5. Composition according to claim 1, characterized in that it contains from 0.5 to 25% by weight of amphiphile constituting the walls of spherules, these percentages being expressed on a weight basis relative to the total weight of the composition.

6. Composition according to claim 1 characterized in that the walls of said spherules contain at least one liposoluble substance selected from the group consisting of a keratolytic agent, an anti-inflammatory agent and an antioxidant agent.

7. Composition according to claim 1, characterized in that the aqueous phase E encapsulated in the spherules is an aqueous solution of an active substance, isoosmotic relative to the phase D which surrounds the spherules.

8. Composition according to claim 7, characterized in that the aqueous phases D and E are identical.

9. Composition according to claim 7, characterized in that the aqueous phase E or the outer aqueous phase D contains at least one water-soluble cosmetic substance taken from the group consisting of humectants, artificial tanning agents, skin coloring agents, antisolar agents, sunscreens, antiperspirant agents, deodorants, astringents, freshening products, tonic products, cicatrizing products, keratolytic products, depilatory products, perfumed waters, water-soluble colorants, antidandruff agents, antiseborrhoeic agents, oxidizing agents, reducing agents and animal or plant tissue extracts.

10. Composition according to claim 7, characterized in that the aqueous phase E or the outer aqueous phase D contains at least one product taken from the group consisting of vitamins, hormones, enzymes, vaccines, antiinflammatories, antibiotics and bactericides.

11. Composition according to claim 1, characterized in that at least on water-immiscible liquid phase L is dispersed in the aqueous phase D.

12. Composition according to claim 11, characterized in that it contains from 2 to 70% by weight of water-immiscible liquid phase L relative to the total weight of the composition, the relative weight proportion of amphiphile lipid constituent of spherules relative to the dispersed water-immiscible liquid phase being between 0.02/1 and 10/1.

13. Composition according to claim 11, characterized in that the water-immiscible liquid phase L dispersed in the aqueous phase D is chosen from the group consisting of esters of fatty acids and of polyols, and esters of fatty acids and of branched alcohols of formula $R_5$—COOR$_6$, in which formula $R_5$ denotes the residue of a higher fatty acid containing from 7 to 19 carbon atoms and $R_6$ denotes a branched hydrocarbon chain containing from 3 to 20 carbon atoms, hexadecane, liquid paraffin or perhydrosqualene, perfluorodecahydronaphthalene, perfluorotributylamine, polysiloxanes, organic acid esters, ethers and polyethers.

14. Composition according to claim 11, characterized in that the phase L contains at least one of a perfume or a liposoluble active substance.

15. Composition according to claim 14, characterized in that the liposoluble substance consists of a sunscreen, a substance intended to improve the condition of dry or senile skins or an antioxidant.

16. Composition according to claim 1, characterized in that the aqueous phase D contains at least one adjuvant taken from the group consisting of opacifiers, gelling agents, flavors, perfumes, sunscreens, and colorants.

17. The composition of claim 1 wherein said nonionic amphiphiles are of natural or synthetic origin, containing, per molecule, one or more hydrophilic groups selected from hydroxyl, ether, carboxyl, phosphate and amine groups.

18. A cosmetic or pharmaceutical composition comprising a dispersion, in an aqueous medium D, suitable for topical application to the skin and nails, of lipidic spherules constituted by organized molecular layers encapsulating an aqueous phase E, the constituent lipid of said layers being nonionic amphiphiles wherein the lipid phase itself of said spherules is combined with at least one lipoprotein free from any sulphydryl functional group, said lipoprotein being selected from a mono- or polyacylated derivative of collegen or hydroxyproline wherein the acyl residue R—CO contains a $C_{13}$–$C_{19}$ hydrocarbon chain, at least one of the functional groups which connects the collagen chain or hydroxyproline residue to the lipophile chain being an amide functional group, it being possible for the carboxylic functional groups of the collagen chain or hydroxyproline residue to be partially or completely neutralized by one or more alkali metal cations, or an ammonium ion or substituted ammonium ion derived from an amine, the said lipoprotein being present in an amount ranging from 1 to 15 percent by weight relative to the total weight of the said lipidic phase itself.

19. A cosmetic or pharmaceutical composition comprising a dispersion, in an aqueous medium D suitable for topical application to the skin and nails, of lipidic spherules constituted by organized molecular layers encapsulating an aqueous phase E, the constituent lipid of said layer being nonionic amphiphiles wherein the lipidic phase itself of said spherules is combined with at least one lipoprotein free from any sulphydryl functional group, said lipoprotein being selected from the group consisting of collagenic palmitoyl lipoamino acid, the O,N-dipalmitoyl derivative of hydroxyproline, hydroxyproline linoleate, sodium steroylglutamate, collagen stearoyl tripeptide, collagen oleoyl tetrapeptide and collagen oleoyl pentapeptide, it being possible for the carboxylic residue functional groups of the collegan chain or hydroxyproline residue of said lipoprotein to be partially or completely neutralized by one or more alkali metal cations, or an ammonium ion or substituted ammonium ion derived from an amine, the said lipoprotein being present in an amount ranging from 1 to 15 percent by weight relative to the total weight of the said lipidic phase itself.

* * * * *